United States Patent [19]

Riebli

[11] Patent Number: 4,859,687
[45] Date of Patent: Aug. 22, 1989

[54] SUBSTITUTED 1,3-DIOXOLANE COMPOUNDS AND THEIR USE AS FUNGICIDES

[75] Inventor: Peter Riebli, Buckten, Switzerland

[73] Assignee: Ciba-Giegy Corporation, Ardsley, N.Y.

[21] Appl. No.: 833,503

[22] Filed: Feb. 20, 1986

Related U.S. Application Data

[63] Continuation of Ser. No. 610,726, May 16, 1984, abandoned.

[30] Foreign Application Priority Data

May 19, 1983 [CH] Switzerland .......................... 2729/83

[51] Int. Cl.[4] .................... C07D 405/06; A61K 31/44
[52] U.S. Cl. ..................................... 514/336; 514/338; 514/345; 514/277; 546/268; 546/270; 546/283; 546/301; 546/302; 546/303; 546/339
[58] Field of Search ................ 546/268, 270, 283, 301, 546/302, 303, 339; 514/336, 338, 345, 277

[56] References Cited

U.S. PATENT DOCUMENTS

| | | | |
|---|---|---|---|
| 4,380,544 | 4/1983 | Dorn | 546/283 |
| 4,443,455 | 4/1984 | Worthington | 514/188 |
| 4,590,198 | 5/1986 | Sugiyama et al. | 546/283 |

FOREIGN PATENT DOCUMENTS

| | | |
|---|---|---|
| 16974 | 11/1980 | European Pat. Off. . |
| 62238 | 3/1982 | European Pat. Off. . |
| 0062238 | 10/1982 | European Pat. Off. . |
| 74018 | 2/1983 | European Pat. Off. . |
| 69330 | 6/1983 | European Pat. Off. . |
| 1296504 | 11/1972 | United Kingdom . |
| 2015524 | 11/1979 | United Kingdom . |

*Primary Examiner*—Jane T. Fan
*Attorney, Agent, or Firm*—Edward M. Roberts; Meredith C. Findlay

[57] ABSTRACT

The described novel pyridine derivatives are those of the general formula I

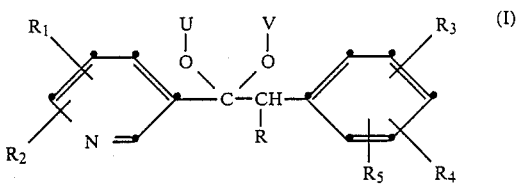

wherein R is hydrogen, $C_1-C_6$-alkyl, $C_3-C_6$-cycloalkyl, phenyl, benzyl, phenyl substituted by $C_1-C_4$-alkyl, halogen, $C_1-C_4$-alkoxy, $NO_2$ and/or $CF_3$, or benzyl substituted by $C_1-C_4$-alkyl, halogen, $C_1-C_4$-alkoxy, $NO_2$ and/or $CF_3$, $R_1$ and $R_2$ independently of one another are each hydrogen, $C_1-C_4$-alkyl, halogen or $C_1-C_4$-alkoxy, $R_3$, $R_4$ and $R_5$ independently of one another are each hydrogen, halogen, $CF_3$, $NO_2$, $C_1-C_4$-alkyl, $C_1-C_4$-alkoxy, phenyl, or phenyl substituted by $C_1-C_4$-alkyl, $C_1-C_4$-alkoxy, halogen, $NO_2$ and/or $CF_3$, U and V independently of one another are each $C_1-C_6$-alkyl, or alkyl substituted by halogen or $C_1-C_4$-alkoxy, or together form one of the following alkylene bridges:

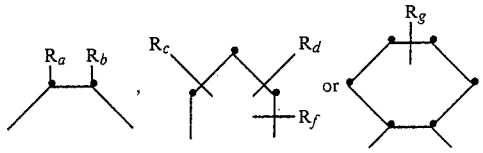

$R_a$ is hydrogen, $C_1-C_{12}$-alkyl, $C_1-C_{12}$-alkyl which is mono- or polysubstituted by halogen, or is phenyl, phenyl which is mono- or polysubstituted by halogen and/or $C_1-C_4$-alkyl, or is the group $-CH_2-Z-R_h$, $R_b$ is $C_1-C_{12}$-alkyl, $C_1-C_{12}$-alkyl which is mono- or polysubstituted by halogen, or is phenyl, phenyl which is mono- or polysubstituted by halogen and/or $C_1-C_4$-alkyl, or is the group $-CH_2-Z-R_h$, wherein Z is oxygen or sulfur, and $R_h$ is hydrogen, $C_1-C_8$-alkyl, $C_1-C_8$-alkyl which is substituted by $C_1-C_4$-alkoxy, or is $C_3-C_4$-alkenyl, 2-propynyl, 3-halo-2-propynyl, phenyl, phenyl which is substituted by halogen, $C_1-C_4$-alkyl, $C_1-C_4$-alkoxy, $NO_2$ and/or $CF_3$, or is benzyl, or benzyl substituted by halogen, $C_1-C_4$-alkyl, $C_1-C_4$-alkoxy, $NO_2$ and/or $CF_3$, $R_c$, $R_d$ and $R_f$ independently of one another are each hydrogen or $C_1-C_4$-alkyl, and $R_g$ is hydrogen or $C_1-C_4$-alkyl; including the acid addition salts thereof.

There is also described the production of these substances, as well as agrochemical compositions containing these substances as active ingredients for controlling phytopathogenic microorganisms.

11 Claims, No Drawings

SUBSTITUTED 1,3-DIOXOLANE COMPOUNDS AND THEIR USE AS FUNGICIDES

This application is a continuation of application Serial No. 610,726, filed May 16, 1984.

The present invention relates to the pyridine derivatives of the formula I defined in the following and to the acid addition salts thereof. It relates also to the production of these compounds as well as to agrochemical compositions containing as active ingredient at least one of the compounds of the formula I; also to the production of these compositions, and to a process for controlling or preventing an infestation of plants by phytopathogenic microorganisms.

The compounds according to the invention are those of the general formula I

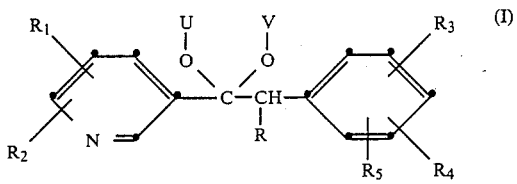

wherein

R is hydrogen, $C_1-C_6$-alkyl, $C_3-C_6$-cycloalkyl, phenyl, benzyl, phenyl substituted by $C_1-C_4$-alkyl, halogen, $C_1-C_4$-alkoxy, $NO_2$ and/or $CF_3$, or benzyl substituted by $C_1-C_4$-alkyl, halogen, $C_1-C_4$-alkoxy, $NO_2$ and/or $CF_3$, $R_1$ and $R_2$ independently of one another are each hydrogen, $C_1-C_4$-alkyl, halogen or $C_1-C_4$-alkoxy, $R_3$, $R_4$ and $R_5$ independently of one another are each hydrogen, halogen, $CF_3$, $NO_2$, $C_1-C_4$-alkyl, $C_1-C_4$-alkoxy, phenyl, or phenyl substituted by $C_1-C_4$-alkyl, $C_1-C_4$-alkoxy, halogen, $NO_2$ and/or $CF_3$, U and V independently of one another are each $C_1-C_6$-alkyl, or alkyl substituted by halogen or $C_1-C_4$-alkyoxy, or together form one of the following alkylene bridges:

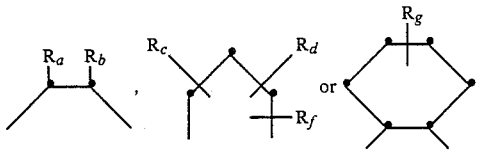

in which $R_a$ is hydrogen, $C_1-C_{12}$-alkyl, $C_1-C_{12}$ alkyl which is mono- or polysubstituted by halogen, or is phenyl, phenyl which is mono- or polysubstituted by halogen and/or $C_1-C_4$-alkyl, or is the group $-CH_2-Z-R_h$, $R_b$ is $C_1-C_{12}$-alkyl, $C_1-C_{12}$-alkyl which is mono- or polysubstituted by halogen, or is phenyl, phenyl which is mono- or polysubstituted by halogen and/or $C_1-C_4$-alkyl, or is the group $-CH_2-Z-R_h$, wherein Z is oxygen or sulfur, and $R_h$ is hydrogen, $C_1-C_8$-alkyl, $C_1-C_8$-alkyl which is substituted by $C_1-C_4$-alkoxy, or is $C_3-C_4$-alkenyl, 2-propynyl, 3-halo-2-propynyl, phenyl, phenyl which is substituted by halogen, $C_1-C_4$-alkyl, $C_1-C_4$-alkoxy, $NO_2$ and/or $CF_3$, or is benzyl, or benzyl substituted by halogen, $C_1-C_4$-alkyl, $C_1-C_4$-alkoxy, $NO_2$ and/or $CF_3$, $R_c$, $R_d$ and $R_f$ independently of one another are each hydrogen or $C_1-C_4$-alkyl, $R_g$ is hydrogen or $C_1-C_4$-alkyl; including the acid addition salts thereof.

By 'alkyl' itself, or as a constituent of another substituent, are meant, depending on the given number of carbon atoms, for example the following groups: methyl, ethyl, propyl, butyl, pentyl, hexyl, heptyl, octyl, nonyl, decyl, undecyl or dodecyl; and isomers thereof, such as: isopropyl, isobutyl, tert-butyl, sec-butyl, isopentyl, and so forth. Alkenyl is for example: propenyl-(1), allyl, butenyl-(1), butenyl-(2) or butenyl-(3). By halogen is meant here and in the following: fluorine, chlorine, bromine or iodine, preferably fluorine, chlorine or bromine.

The invention relates both to the free compounds of the formula I and to the addition salts thereof with organic and inorganic acids.

Examples of salt-forming acids are: inorganic acids: hydrohalic acids, such as hydrofluoric acid, hydrochloric acid, hydrobromic acid or hydriodic acid, as well as sulfuric acid, phosphoric acid, phosphorous acid or nitric acid; and organic acids, such as acetic acid, trifluoroacetic acid, trichloroacetic acid, propionic acid, tartaric acid, glycolic acid, thiocyanuric acid, lactic acid, succinic acid, citric acid benzoic acid, cinnamic acid, oxalic acid, formic acid, benzenesulfonic acid, p-toluenesulfonic acid, methanesulfonic acid, salicylic acid, p-aminosalicyclic acid, 2- phenoxybenzoic acid or 2-acetoxybenzoic acid.

The compounds of the formula I at room temperature are stable oils, resins or solids, which are distinguished by very valuable microbicidal properties, particularly phytofungicidal properties. The compounds can therefore be used in agriculture or in related fields for controlling phytopathogenic microorganisms.

A preferred group of microbicides is formed by compounds of the formula I wherein R is hydrogen or methyl, $R_1$ and $R_2$ independently of one another are each hydrogen, methyl, ethyl, fluorine, chlorine, bromine or methoxy; $R_3$, $R_4$ and $R_5$ independently of one another are each hydrogen, fluorine, chlorine, bromine, $CF_3$, $NO_2$, methyl or methoxy, U and V independently of one another are each $C_1-C_3$-alkyl, or together form the following alkylene bridge

in which $R_a$ is hydrogen, $C_1-C_4$-alkyl, phenyl, or phenyl which is mono- to trisubstituted by fluorine, chlorine, bromine and/or methyl, or is the group $-CH_2-Z-R_h$, $R_b$ is $C_1-C_4$-alkyl, or $C_1-C_4$-alkyl which is mono- to trisubstituted by fluorine, chlorine and/or bromine, or is phenyl, or phenyl which is mono- to trisubstituted by fluorine, chlorine, bromine and/or methyl, or is the group $-CH_2-Z-R_h$, wherein Z is oxygen or sulfur, and $R_h$ is hydrogen, $C_1-C_6$-alkyl, $C_1-C_3$-alkyl which is substituted by $C_1-C_4$-alkoxy, or is $C_3-C_4$-alkenyl, 2-propynyl, 3-halo-2-propynyl, phenyl, or phenyl substituted by fluorine, chlorine, bromine, methyl, methoxy, nitro and/or $CF_3$, or is benzyl, or benzyl substituted by fluorine, chlorine, bromine, methyl, methoxy, $NO_2$ and/or $CF_3$; including the acid addition salts thereof.

These compounds are to be designated here and in the following as subgroup Ia.

A further preferred group of microbicides is formed by compounds of the formula I wherein R is hydrogen or methyl, $R_1$ and $R_2$ independently of one another are each hydrogen, methyl, ethyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy, U and V independently of one another are each $C_1$–$C_3$-alkyl, or together form the following alkylene bridge

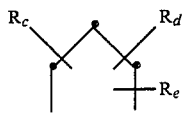

wherein $R_c$, $R_d$ and $R_e$ independently of one another are each hydrogen or $C_1$–$C_4$-alkyl, and the total number of carbon atoms in $R_c$, $R_d$ and $R_e$ does not exceed 6; including the acid addition salts thereof.

This subgroup is to be designated here and in the following as subgroup Ib.

A preferred group of microbicides is formed also by compounds of the formula I wherein R is hydrogen or methyl, $R_1$ and $R_2$ independently of one another are each hydrogen, methyl, ethyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy, U and V independently of one another are each $C_1$–$C_3$-alkyl, or together form the following alkylene bridge

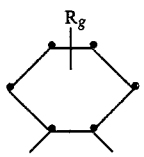

in which $R_g$ is hydrogen or $C_1$–$C_4$-alkyl; including the acid addition salts thereof.

This subgroup is to be designated here and in the following as subgroup Ic.

A particularly preferred group of microbicides is formed by compounds of the formula I wherein R is hydrogen, $R_1$ and $R_2$ independently of one another are each hydrogen, methyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy, U and V together form the following alkylene bridge:

in which $R_a$ is hydrogen and methyl, and $R_b$ is $C_1$–$C_4$-alkyl, or $C_1$–$C_4$-alkyl substituted by fluorine, chlorine or bromine, or is phenyl, or phenyl which is mono- to trisubstituted by fluorine, chlorine, bromine and/or methyl, or is the group —$CH_2$—Z—$R_h$, in which Z is oxygen or sulfur, and $R_h$ is hydrogen, $C_1$–$C_4$-alkyl, or $C_1$–$C_2$-alkyl substituted by $C_1$–$C_4$-alkoxy, or is $C_3$–$C_4$-alkenyl, 2-propynyl, 3-halo-2-propynyl, phenyl, or phenyl substituted by fluorine, chlorine, bromine, methyl, methoxy, nitro and/or $CF_3$, or is benzyl, or benzyl substituted by fluorine, chlorine, bromine, methyl, methoxy, nitro and/or $CF_3$.

This important subgroup is to have here and in the following the designation Id.

A further particularly preferred group of microbicides is formed by compounds of the formula I wherein R is hydrogen, $R_1$ and $R_2$ independently of one another are each hydrogen, methyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy, U and V together form the alkylene bridge:

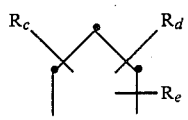

in which $R_c$ is hydrogen, and $R_d$ and $R_e$ independently of one another are each hydrogen, methyl or ethyl.

This subgroup is to be designated here and in the following as subgroup Ie.

Another especially preferred group of microbicides is formed by compounds of the formula I wherein R is hydrogen, $R_1$ and $R_2$ independently of one another are each hydrogen, methyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy, and U and V together form the following alkylene bridge:

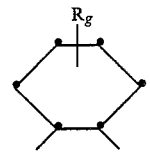

in which $R_g$ is hydrogen, methyl or ethyl.

This subgroup is to be designated here and in the following as subgroup If.

Most particularly preferred by virtue of their marked microbicidal action are for example the following individual substances, as isomeric mixtures or in the optically pure form:

3-[2-(2,4-dichlorobenzyl)-4-methoxymethyl-1,3-dioxolan-2-yl]-pyridine,

3-[2-(2,4-dichlorobenzyl)-4-methyl-1,3-dioxolan-2-yl]-pyridine,

3-[2-(2,4-dichlorobenzyl)-4-chloromethyl-1,3-dioxolan-2-yl]-pyridine,

3-[2-(2,4-dichlorobenzyl)-1,3-dioxan-2-yl]-pyridine,

3-[2-(2,4-dichlorobenzyl)-4-hydroxymethyl-1,3-dioxolan-2-yl]-pyridine, and

3-[2-(2,4-dichlorobenzyl)-4-ethyl-1,3-dioxolan-2-yl]-pyridine.

The compounds of the formula I can be produced by a whole series of reaction variants A to E. The individual variants are subsequently described in detail. The substituents R, $R_1$, $R_2$, $R_3$, $R_4$, $R_5$, U, V, $R_a$, $R_b$, $R_c$, $R_d$, $R_e$, $R_f$, $R_g$ and $R_h$ in the starting products and in the intermediates have in the following the meanings defined under the formula I.

The procedures for the reaction variants A to E can be as follows:

A. Ketals of the formula I can be produced by a ketalisation reaction of a ketone of the formula II

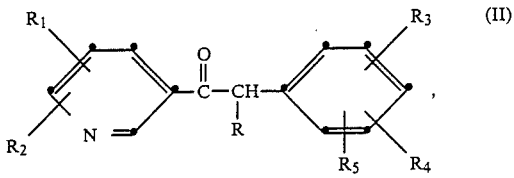

in the presence of an acid, with an alcohol V—OH or U—OH, with a diol of the formula HO—U—V—OH or with an orthocarboxylic acid ester R'—C(OV)$_3$ or R'—C(OU)$_3$, or by transketalisation of the resulting ketal with an excess of the corresponding alkanol or diol, the substituents R to R$_5$, U and V in the formula II, as well as in the alcohols and diols, having the meanings defined under the formula I, and R' being preferably a lower alkyl group.

This ketalisation reaction can be performed analogously to ketalisation reactions already known, for example by a process analogous to that for the production of 2-bromomethyl-2,4-diphenyl-1,3-dioxolane [Synthesis, 1974, (I), 23].

The preferred method of carrying out the ketalisation reaction comprises refluxing both reactants for several hours, together with an azeotrope-former, in one of the customary organic solvents. Suitable azeotrope-formers are for example: benzene, toluene, xylene, chloroform or carbon tetrachloride; and to accelerate the reaction an addition of a strong acid, for example p-toluenesulfonic acid, can be advantageous. Organic solvents which can be used in this case are, for example, aromatic hydrocarbons, such as benzene, toluene, xylene, and so forth, and saturated hydrocarbons, such as n-hexane.

B. Especially when, in compounds of the formula I, the substituents U and V together are —CH$_2$—CH(CH$_2$ZR$_h$)—, these compounds can be produced by reaction of a compound of the formula III

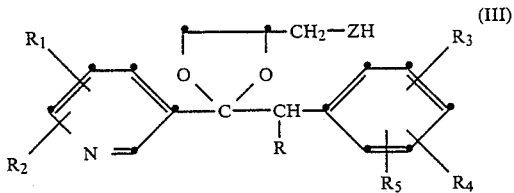

with a reactive compound of the formula IV suitable for O-alkylation or S-alkylation:

the substituents R to R$_5$, R$_h$ and Z in the formulae III and IV having the meanings defined under the formula I, and X being one of the customary removable groups, for example halogen, especially chlorine, bromine or iodine, or benzenesulfonyloxy, p-tosyloxy, trifluoroacetyloxy or preferably lower alkylsulfonyloxy, such as mesyloxy.

The reaction is preferably performed in inert organic solvents. Suitable for this purpose are for example: N,N-dimethylformamide, N,N-dimethylacetamide, hexamethylphosphorus triamide, dimethyl sulfoxide, 4-methyl-2-pentanone, and so forth. It is also possible to use mixtures with other reactive solvents, for example with aromatic hydrocarbons, such as benzene, toluene, xylene, and the like. To accelerate the rate of reaction, it can in some cases prove advantageous to perform the reaction in the presence of a base. Such bases are for example alkali metal hydrides or alkali metal carbonates. It can also be of advantage in certain cases to firstly convert the compound III, in a known manner, into a suitable metal salt. This is effected preferably by reaction of III with an Na compound, for example sodium hydride, sodium hydroxide, and so forth. This salt of III is subsequently reacted with the compound of the formula IV. In order to increase the rate of reaction, the reaction can in some cases be performed also at elevated temperature, preferably at 80° to 130° C., or at the boiling point of the solvent.

C. Compounds of the formula I in which -U---V- is —CH$_2$—CH(CH$_2$—Z—R$_h$) can also be produced by reacting a ketal of the formula V

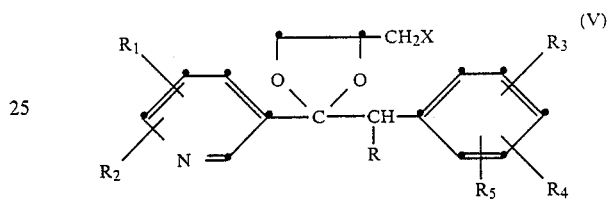

with a compound of the formula VI $$R_h-Z-M \qquad (VI),$$

wherein the substituents R to R$_5$, R$_h$ and Z have the meanings defined under the formula I, X has the meanings given in variant B, and M is hydrogen or preferably a metal atom, especially an alkali metal atom.

D. When Z in the products of the formula I is oxygen, these compounds are obtainable also by a condensation reaction of an alcohol of the formula VII with an alkanol of the formula VIII

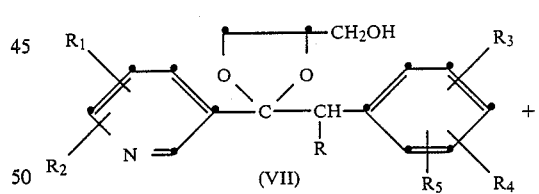

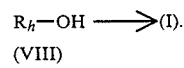

The substituents R to R$_5$ and R$_h$ have here the meanings defined under the formula I.

In this condensation reaction, the reactants can be heated in a suitable solvent under refluxing conditions, the formed water being simultaneously distilled off azeotropically from the reaction mixture. Suitable solvents are aromatic hydrocarbons, such as toluene or the alcohol VIII itself. This reaction is performed advantageously in the presence of a strong acid, for example p-toluenesulfonic acid.

E. The introduction of the substituent R into an unbranched product of the formula I'

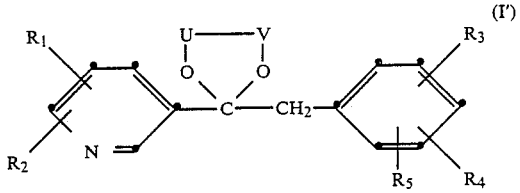
(I')

can be effected by reaction thereof with a compound of the formula IX

the substituents R to $R_5$ and U and V in the formulae I' and IX having the meanings defined under the formula I and X being a customary removable group as given in variant B. This reaction is performed advantageously under the conditions described in variant B, the compound of the formula I' being preferably firstly converted, before the reaction with IX, into a metal salt, especially an alkali metal salt. This is carried out for example analogously to the reactions of III in variant B.

When the compounds of the formula I are obtained as bases, these can be converted by inorganic or organic acids into corresponding salts of the formula I. Conversely, salts of the formula I can be converted, for example by reaction with alkali(hydrogen)carbonate or alkali hydroxide, into the free bases of the formula I.

The starting ketones of the formula II can be produced, using methods known per se, for example by reacting a benzyl halide of the formula X

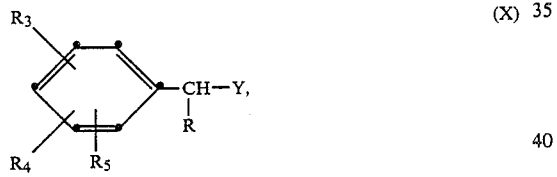

wherein R to $R_5$ have the meanings defined under the formula I, and Y is halogen, preferably chlorine, bromine or iodine, with a pyridine derivative of the formula XI

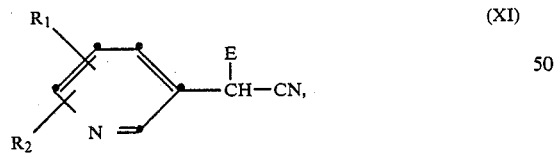

wherein $R_1$ and $R_2$ have the meanings defined under the formula I, and E is a disubstituted amino radical, for example dimethylamino, diethylamino, piperidino, morpholino, and so forth, to give a compound of the formula XII

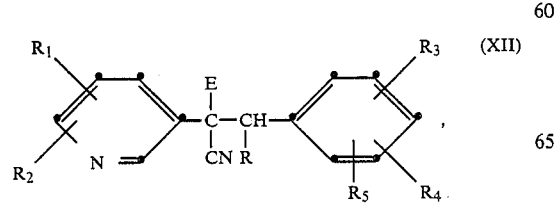

and hydrolysing this.

The compounds of the formulae V—OH, U—OH, HO—U—V—OH, R'—C(OV)$_3$, R'—C(OU)$_3$, IV, VI, VIII and IX are generally known or are produced by methods known per se. The production of the intermediates.

The starting materials of the formulae III, V and VII, which were specially developed for the production of the compounds of the formula I according to the invention, are novel and likewise form subject matter of the invention; they too moreover have microbicidal properties.

The production variants described are a part of the present invention.

In the described ketalisation reactions of a ketone with a substituted $\alpha,\beta$- or $\alpha,\gamma$- diol, there are principally formed mixtures of diastereoisomers of the resulting ketal. Correspondingly, diastereoisomeric mixtures of the final products I are in general formed from the starting ketones. The compounds of the formula I can be for example in the following two diastereoisomeric forms:

A types

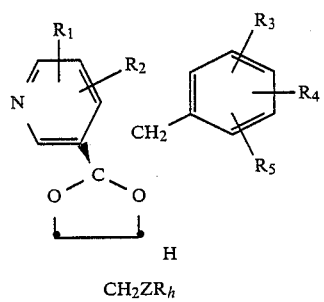

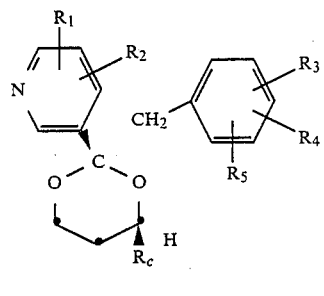

The configuration of type A is to be denoted, here and in the following, as the "trans" isomer.

B types

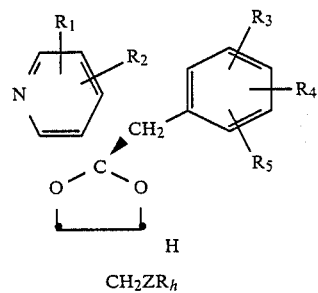

-continued
B types

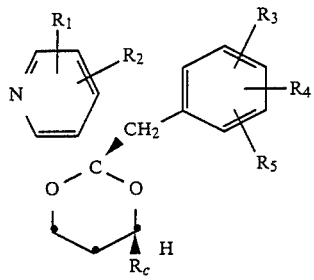

The symbols in the structures reproduced three-dimensionally have the following meanings:

| ... = | behind |
| = | in |
| = | in front of the drawing plane. |

The configuration of type B is accordingly to be denoted as the "cis" isomer. The separation of the two diastereoisomers can be performed for example by fractional crystallisation or by chromatography (thin-layer, thick-layer, column or liquid-high-pressure chromatography, and so forth). The two isomers exhibit differing microbicidal activity. The diastereoisomeric mixtures are in general used for practical purposes.

The invention embraces all isomeric compounds of the formula I, and the salts and metal complexes thereof.

In its described variants A, B, C, D and E, the production process to obtain compounds of the formula I is part of the present invention.

Some of the starting materials and intermediates used in the process variants A, B, C, D and E are known, others can be produced by methods known per se. Some however are novel, and the production thereof is described herein.

It has been established that compounds of the formula I surprisingly exhibit for practical purposes a very favourable microbicidal spectrum against phytopathogenic fungi and bacteria. They have very advantageous curative, preventive and systemic properties, and can be used for the protection of cultivated plants. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms.

The active substances of the formula I are effective against the phytopathogenic fungi belonging to the following classes: Ascomycetes (for example Venturia, Podosphaera, Erysiphe, Monilinia and Uncinula); Basidiomycetes (for example the species: Hemileia, Rhizoctonia and Puccinia); Fungi imperfecti (for example Botrytis, Helminthosporium, Fusarium, Septoria, Cercospora and Alternaria). Furthermore, the compounds of the formula I have a systemic action. They can also be used as dressing agents for treating seed (fruit, tubers and grain), and plant cuttings to protect them from fungus infections, and also against phytopathogenic fungi occurring in the soil. The active substances according to the invention are distinguished also by a particularly good tolerance to plants. Surprisingly, the compounds of the formula I according to the invention exhibit, compared with the compounds unsubstituted in the dioxolane ring, not only a better plant tolerance—even with higher applied amounts—but also a broader spectrum of activity, and in addition they have in smaller applied amounts an action which meets practical requirements to a greater extent.

The invention relates also to microbicidal compositions containing compounds of the formula I, and to the use thereof for controlling phytopathogenic microorganisms, especially fungi which damage plants, and/or for preventing an infestation of plants.

The present invention also includes the production of agrochemical compositions, which is characterised by the intimate mixing of the active ingredient with one or more substances or groups of substances described herein. Also included is a process for the treatment of plants, which process comprises the application of compounds of the formula I or of the novel compositions.

Within the scope of this invention, target crops with respect to the range of indications disclosed herein include for example the following species of cultivated plants: cereals: (wheat, barley, rye, oats, rice, sorghum and related cereals); beet: (sugar beet and fodder beet); pomaceous fruit, stone fruit and soft fruit: (apples, pears, plums, peaches, almonds, cherries, strawberries, raspberries, and blackberries); legumes: (beans, lentils, peas and soya-bean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabbage, carrots, onions, tomatoes, potatoes and paprika); laurel plants: (avocado, cinnamon and camphor); or plants such as maize, tobacco, nuts, coffee, sugar beet, tea, grapevines, hops, bananas and natural rubber plants, as well as ornamental plants (composites).

Active substances of the formula I are customarily used in the form of compositions, and can be applied, simultaneously or successively, with further active substances to the area or plants to be treated. These further active substances can be fertilisers, traceelement agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilizers.

A preferred method of applying an active substance of the formula I, or an agrochemical composition containing at least one of these active substances, is application to the foliage (leaf application). The number of applications and the amounts applied are governed by the extent of infestation with respect to the pathogen (fungus genus) concerned. The active substances of the formula I can however be fed into the plant through the soil and then by way of the root system (systemic action), this being achieved by the locus of the plant being soaked with a liquid preparation, or by the substances being introduced in solid form into the soil, for example in the form of a granulate (soil application). The compounds of the formula I can also be applied to the seed grains (coating), the grains being for this purpose either soaked with a liquid preparation of the active substance or coated with a solid preparation. Further forms of application are possible in special cases, for example the specific treatment of the stalks or buds of the plants.

The compounds of the formula I are used either in an unmodified form or preferably together with auxiliaries customarily employed in formation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

The formulations, that is to say, the compositions or preparations containing the active substance of the formula I and optionally a solid or liquid additive, are produced in a known manner, for example by the intimate mixing and/or grinding of the active substance with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acid or highly dispersed absorbent polymers. Suitable granulated adsorptive carriers are porous types, for example pumice, ground brick, sepiolite or bentonite; and suitable non-sorbent carriers are materials such as calcite or sand. There can also be used a great number of pre-granulated materials of inorganic or organic nature, such as in particular dolomite or ground plant residues.

Particularly advantageous additives facilitating application and rendering possible a marked reduction in the amount of active substance applied are moreover natural (animal or vegetable) or synthetic phospholipides from the class comprising the cephalins and lecithins, for example phosphatidylethanolamine, phosphatidylserine, phasphatidylcholine, sphingomyelin, phosphatidylinosite, phosphatidyl glycerol, lysolecithin, plasmalogenes or cardiolipin, which can be obtained for example from animal or plant cells, especially from the brain, heart, liver, egg yokes or soya beans. Applicable commercial mixtures are for example phosphatidylcholine mixtures. Synthetic phospholipides are for example dioctanoylphosphatidylcholine and dipalmitoylphosphatidylcholine.

Depending on the nature of the active ingredient of the formula I to be formulated, suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Including among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, or dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ethyl groups, with polypropylene glycol, ethylenediaminolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)-ethylammonium bromide.

The tensides customarily used in formulation practice are described, inter alia, in the following publications:
"Mc Cutcheon's Detergents and Emulsifiers Annual" MC Publishing Corp., Ridgewood, N.J., 1981;
Dr. Helmut Stache "Tensid-Taschenbuch" (Tenside Handbook) Carl Hanser Verlag, Munich/Vienna, 1981.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside.

Whereas commercial products are preferably in the form of concentrated compositions, the compositions employed by the end-user are as a rule diluted.

The compositions can also contain additives such as stabilisers, antifoaming agents, viscosity regulators, binders and adhesives, as well as fertilisers or other active ingredients for obtaining special effects.

Agrochemical compositions of the types described herein likewise form part of the present invention.

The following Examples serve to further illustrate the invention without limiting the scope thereof. Percentage values and 'parts' relate to weight. RT denotes room temperature, and h signifies 'hour'.

PRODUCTION EXAMPLES

Example P1: Production of

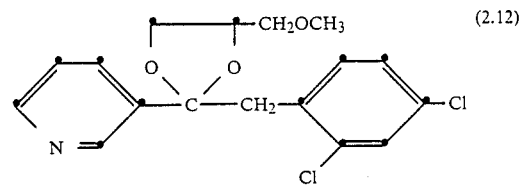
(2.1)

3-[2-(2,4-Dichlorobenzyl)-4-methyl-1,3-dioxolan-2-yl] pyridine 13.3 g of 2,4-dichlorobenzyl-3-pyridyl ketone, 7.6 g of propanediol-1,2 and 13.0 g of p-toluenesulfonic acid are boiled in 150 ml of xylene for 32 h in a water separator. After cooling to RT, the reaction mixture is poured into 600 ml of 2N sodium hydroxide solution, and extracted 3 times with 200 ml of ether each time. The combined organic phases are washed with 250 ml of water, dried over sodium sulfate and filtered. The solvent is evaporated off and the oily crude product is purified by column chromatography (eluant: ether). The compound is obtained as clear colourless oil; $n_D^{22.5}$:1.5676.

Example P2: Production of

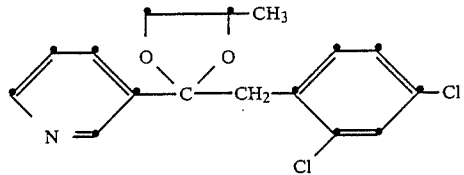
(2.12)

3-[2-(2,4-Dichlorobenzyl)-4-methoxymethyl-1,3-dioxolan-2yl] pyridine 6.0 g of 3-[2-(2,4-dichlorobenzyl)-4-chloromethyl-1,3-dioxolan-2-yl] pyridine, 1.8 g of sodium methylate and a catalytically acting amount of sodium iodide are stirred in 50 ml of dimethyl sulfoxide for 20 h at an internal temperature of +120° C. After cooling to RT, the reaction mixture is poured into 400 ml of water, and extracted twice with 120 ml of ethyl acetate each time. The organic phases are combined, washed with 150 ml of water, dried over sodium sulfate, treated with active charcoal and filtered, and the solvent is evaporated off. The oily residue is purified by chromatography on silica gel with ether. The compound is obtained as colourless oil; $n_D^{22.5}$:1.4774.

There can be obtained in an analogous manner also the following final products of the formula I (except where otherwise stated, they are diastereoisomeric mixtures having differing mixture ratios).

TABLE 1

Compounds of the formula

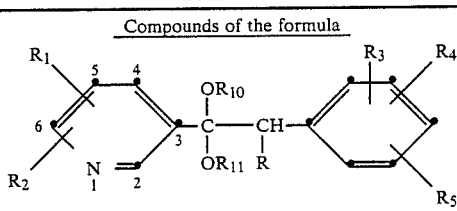

| Comp. No. | $R_1$ | $R_2$ | $R_{10}$ | $R_{11}$ | R | $R_3$ | $R_4$ | $R_5$ | Salt |
|---|---|---|---|---|---|---|---|---|---|
| 1.1 | H | H | $CH_3$ | $CH_3$ | H | 2-Cl | 4-Cl | H | — |
| 1.2 | 2-Cl | H | $CH_3$ | $CH_3$ | $CH_3$ | 2-Cl | 4-Cl | H | — |
| 1.3 | H | 6-Cl | $CH_3$ | $CH_3$ | H | 2-Cl | 4-Cl | H | — |
| 1.4 | 2-Cl | H | $CH_3$ | $CH_3$ | H | 2-Cl | 4-Cl | H | — |
| 1.5 | 2-Cl | H | $C_2H_5$ | $C_2H_5$ | $C_3H_7$—n | 2-Cl | 4-Cl | H | $HNO_3$ |
| 1.6 | H | 6-$OCH_3$ | $CH_3$ | $CH_3$ | H | 2-Cl | 4-Cl | H | — |
| 1.7 | 2-Cl | H | $C_2H_5$ | $C_2H_5$ | H | 2-F | H | H | — |
| 1.8 | 2-Cl | H | $CH_3$ | $CH_3$ | H | H | 4-F | H | — |
| 1.9 | H | 6-$CH_3$ | $CH_3$ | $CH_3$ | H | 2-Cl | 4-Cl | H | — |
| 1.10 | H | 6-$CH_3$ | $C_2H_5$ | $C_2H_5$ | H | H | 4-Cl | H | — |
| 1.11 | H | 6-$CH_3$ | $CH_3$ | $CH_3$ | $CH_3$ | H | 4-F | H | — |
| 1.12 | H | 6-$CH_3$ | $CH_3$ | $CH_3$ | $C_6H_5$ | 2-Cl | 4-Cl | 6-Cl | — |

TABLE 1-continued

Compounds of the formula

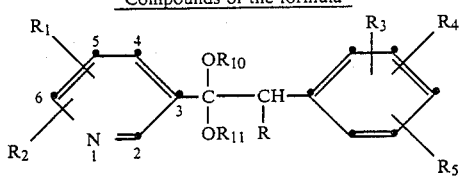

| Comp. No. | $R_1$ | $R_2$ | $R_{10}$ | $R_{11}$ | R | $R_3$ | $R_4$ | $R_5$ | Salt |
|---|---|---|---|---|---|---|---|---|---|
| 1.13 | 2-Cl | H | $CH_3$ | $CH_3$ | H | H | 4-$CH_3$ | H | — |
| 1.14 | H | 6-Cl | $CH_3$ | $CH_3$ | H | H | 4-$CH_3$ | H | — |
| 1.15 | H | 6-$OCH_3$ | $CH_3$ | $CH_3$ | $CH_3$ | H | 3-$CF_3$ | H | HCl |
| 1.16 | H | 6-$CH_3$ | $C_2H_5$ | $C_2H_5$ | H | H | 3-$CF_3$ | H | — |
| 1.17 | H | H | $CH_3$ | $CH_3$ | H | H | 3-$CF_3$ | H | — |
| 1.18 | 2-Cl | H | $CH_3$ | $CH_3$ | $CH_2C_6H_5$ | 2-Cl | 4-Cl | H | — |
| 1.19 | H | H | $CH_3$ | $CH_3$ | 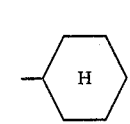 | 2-Cl | 4-Cl | H | — |
| 1.20 | H | H | $CH_3$ | $CH_3$ | H | H | 4-$C_6H_5$ | H | — |
| 1.21 | H | 6-$OCH_3$ | $C_2H_5$ | $C_2H_5$ | H | H | 4-$NO_2$ | H | — |
| 1.22 | H | H | $C_2H_5$ | $C_2H_5$ | H | 2-Cl | 4-Cl | H | — |
| 1.23 | H | H | $CH_3$ | $CH_3$ | $CH_3$ | 2-Cl | 4-Cl | H | — |

TABLE 2

Compounds of the formula

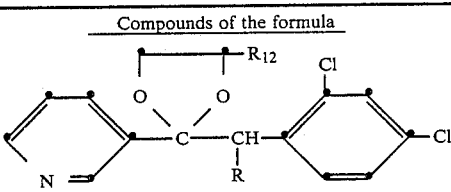

including all isomeric forms

| Comp. No. | $R_{12}$ | R | Salt | Physical constants |
|---|---|---|---|---|
| 2.1 | $CH_3$ | H | — | $n_D^{22,5}$: 1,5676 |
| 2.2 | $CH_3$ | $CH_3$ | $HNO_3$ | |
| 2.3 | $CH_3$ | $CH_3$ | HCl | |
| 2.4 | $CH_3$ | $CH_3$ | — | |
| 2.5 | $CH_3$ | $CH_2C_6H_5$ | $(COOH)_2$ | |
| 2.6 | $C_2H_5$ | H | — | $n_D^{24,5}$: 1,5651 |
| 2.7 | $C_2H_5$ | H | $(COOH)_2$ | |
| 2.8 | $C_2H_5$ | $CH_3$ | — | |
| 2.9 | $C_3H_7$—i | H | — | |
| 2.10 | $C_3H_7$—n | H | — | |
| 2.11 | $C_3H_7$—n | $C_2H_5$ | — | |
| 2.12 | $CH_2OCH_3$ | H | — | $n_D^{22,5}$: 1,4774 |
| 2.13 | $CH_2OCH_3$ | $CH_3$ | — | |
| 2.14 | $CH_2OCH_3$ | $C_6H_5$ | — | |
| 2.15 | $CH_2OC_2H_5$ | H | — | |
| 2.16 | $CH_2OH$ | H | — | $n_D^{26}$: 1,5651 |
| 2.17 | $CH_2OH$ | H | $CCl_3COOH$ | |
| 2.18 | $CH_2OC_6H_5$ | H | — | |
| 2.19 | $CH_2OCH_2CH=CH_2$ | H | — | |
| 2.20 | $C_3H_7$—n | H | $HNO_3$ | |
| 2.21 | $C_4H_9$—n | H | — | |
| 2.22 | $CH_2OCH_2CH=CH_2$ | $CH_3$ | — | |
| 2.23 | $CH_2OCH_2CH=CH_2$ | 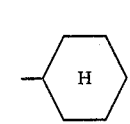 | — | |
| 2.24 | $CH_2OC_6H_5$ | $C_3H_7$—n | — | |
| 2.25 | $CH_2Cl$ | H | — | $n_D^{22,5}$: 1,5703 |
| 2.26 | $CH_2Cl$ (trans) | H | — | $n_D^{21}$: 1,5688 |
| 2.27 | $CH_2Cl$ (cis) | H | — | $n_D^{21}$: 1,5736 |
| 2.28 | $CH_2Cl$ | $CH_3$ | — | $n_D^{22}$: 1,5656 |

TABLE 2-continued

Compounds of the formula

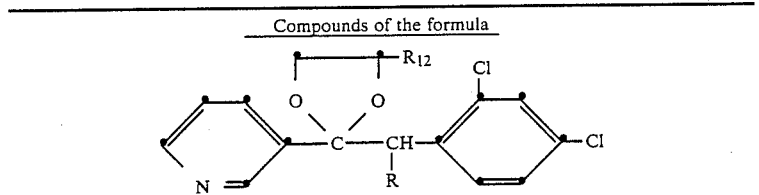

including all isomeric forms

| Comp. No. | $R_{12}$ | R | Salt | Physical constants |
|---|---|---|---|---|
| 2.29 | $CH_2Cl$ | $C_6H_5$ | | |
| 2.30 | $CH_2Cl$ | (cyclopropyl) | — | |
| 2.31 | $CH_2Cl$ | $CH_2(C_6H_3Cl_2-2,4)$ | — | |
| 2.32 | $CH_2CH_3$ | $C_4H_9-t$ | — | |
| 2.33 | $CH_2Cl$ | H | HCl | |
| 2.34 | $CH_2Cl$ | $C_2H_5$ | — | resin |
| 2.35 | $CH_2Cl$ | $C_3H_7-n$ | — | resin |
| 2.36 | $CH_2Cl$ | $CH_2C_6H_5$ | — | resin |
| 2.37 | $CH_2Br$ | H | — | resin |
| 2.38 | $CH_2OH$ | $CH_3$ | — | resin |
| 2.39 | $CH_2Cl$ (trans) | $CH_3$ | — | $n_D^{22}$: 1,5623 |
| 2.40 | $CH_2Cl$ (cis) | $CH_3$ | — | $n_D^{22}$: 1,5675 |

TABLE 3

Compounds of the formula

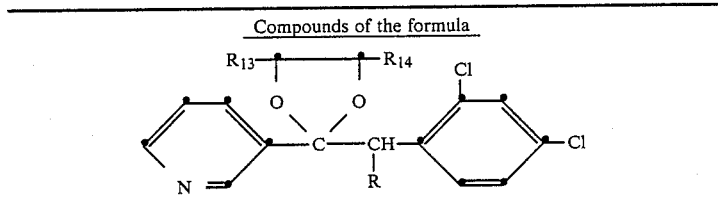

including the isomeric forms thereof

| Comp. No. | $R_{13}$ | $R_{14}$ | R | Salt | Physical constants |
|---|---|---|---|---|---|
| 3.1 | $CH_3$ | $C_2H_5$ | H | — | |
| 3.2 | $CH_3$ | $C_2H_5$ | $CH_3$ | — | |
| 3.3 | $CH_3$ | $C_2H_5$ | H | $HNO_3$ | |
| 3.4 | $CH_3$ | $C_3H_7-n$ | H | — | |
| 3.5 | $CH_3$ | $C_3H_7-n$ | $CH_3$ | — | |
| 3.6 | $CH_3$ | $C_2H_5$ | $C_2H_5$ | HCl | |
| 3.7 | $CH_3$ | $CH_3$ | H | — | resin |
| 3.8 | $CH_3$ | $CH_3$ | $CH_3$ | — | resin |
| 3.9 | $C_2H_5$ | $C_3H_7-n$ | H | — | |
| 3.10 | $C_2H_5$ | $C_3H_7-i$ | H | — | |
| 3.11 | $C_2H_5$ | $C_2H_5$ | H | — | |
| 3.12 | $CH_3$ | $C_2H_5$ | $C_6H_5$ | — | |
| 3.13 | $CH_3$ | $C_2H_5$ | $CH_2C_6H_5$ | — | |
| 3.14 | $CH_3$ | $C_2H_5$ | cyclohexyl | — | |
| 3.15 | $CH_3$ | $C_3H_7-i$ | $C_6H_5$ | $(COOH)_2$ | |
| 3.16 | $CH_3$ | $C_2H_5$ | $C_3H_7-n$ | — | |
| 3.17 | $CH_3$ | $CH_3$ | (cyclopropyl) | — | |
| 3.18 | $CH_3$ | $CH_3$ | $C_3H_7-i$ | — | |
| 3.19 | $-(CH_2)_4-$ | | H | — | |
| 3.20 | $-(CH_2)_4-$ | | $CH_3$ | — | |
| 3.21 | $-(CH_2)_4-$ | | $C_6H_5$ | — | |
| 3.22 | $-(CH_2)_4-$ | | H | HCl | |

TABLE 4

Compounds of the formula

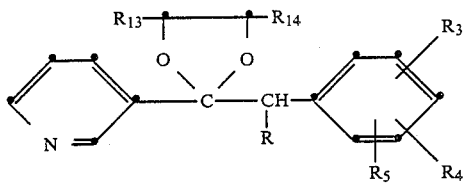

including the isomeric forms thereof

| Comp. No. | $R_{13}$ | $R_{14}$ | R | $R_3$ | $R_4$ | $R_5$ | Salt |
|---|---|---|---|---|---|---|---|
| 4.1 | H | $CH_3$ | H | 3-Cl | 4-Cl | H | — |
| 4.2 | H | $CH_3$ | H | 3-Cl | 4-Cl | H | HCl |
| 4.3 | $CH_3$ | $CH_3$ | H | 3-$NO_2$ | H | H | — |
| 4.4 | $CH_3$ | $C_2H_5$ | H | 3-$CF_3$ | H | H | — |
| 4.5 | H | $CH_3$ | $CH_3$ | 2-Cl | H | H | — |
| 4.6 | H | $CH_2Cl$ | H | 3-F | H | H | — |
| 4.7 | H | $CH_2Cl$ | $CH_3$ | 2-Br | 4-Br | H | — |
| 4.8 | H | $CH_2OCH_3$ | H | 2-F | H | H | — |
| 4.9 | H | $CH_2OCH_3$ | H | H | 3-$CF_3$ | H | — |
| 4.10 | H | $CH_2OCH_3$ | H | H | 4-F | H | — |
| 4.11 | H | $CH_2OCH_3$ | H | H | 4-Cl | H | — |
| 4.12 | H | $CH_2Cl$ | H | H | 4-$C_6H_5$ | H | — |
| 4.13 | H | $CH_2Cl$ | H | H | H | H | — |
| 4.14 | H | $CH_2OH$ | $CH_3$ | H | 4-Cl | H | — |
| 4.15 | H | $CH_2OH$ | H | H | 4-F | H | — |
| 4.16 | H | $CH_2OH$ | $CH_3$ | H | 4-$CH_3$ | H | — |
| 4.17 | H | $CH_2OH$ | $C_6H_5$ | 2-Cl | 4-Cl | 6-Cl | $(COOH)_2$ |
| 4.18 | H | $CH_2OC_6H_5$ | H | H | 4-F | H | — |
| 4.19 | H | $CH_2OCH_2CH=CH_2$ | $CH_3$ | H | 4-Cl | H | — |
| 4.20 | H | $CH_2Cl$ | $C_6H_5$ | H | 4-$CH_3$ | H | — |
| 4.21 | H | $CH_2Cl$ | $CH_2C_6H_5$ | H | 4-F | H | — |
| 4.22 | H | $CH_2Cl$ | H | 3-$CF_3$ | H | H | — |
| 4.23 | —$(CH_2)_4$— | | H | H | 4-Cl | H | — |
| 4.24 | —$(CH_2)_4$— | | $CH_3$ | H | 4-Cl | H | — |
| 4.25 | —$(CH_2)_4$— | | $C_3H_7$—n | H | 4-F | H | — |
| 4.26 | —$(CH_2)_4$— | | $C_6H_5$ | H | 3-$CF_3$ | H | — |

TABLE 5

Compounds of the formula

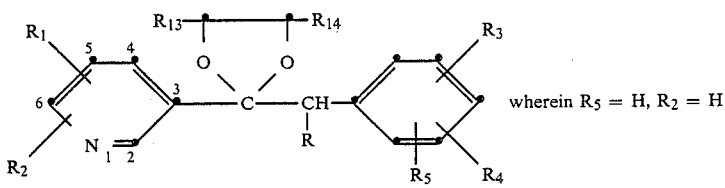

wherein $R_5$ = H, $R_2$ = H

| Comp. No. | $R_1$ | $R_{13}$ | $R_{14}$ | $R_3$ | $R_4$ | R | Salt | Physical constants |
|---|---|---|---|---|---|---|---|---|
| 5.1 | 2-Cl | H | $CH_3$ | 2-Cl | 4-Cl | H | — | |
| 5.2 | 2-Cl | $CH_3$ | $CH_3$ | H | 4-Cl | H | — | |
| 5.3 | 2-Cl | $CH_3$ | $C_2H_5$ | H | 4-F | $CH_3$ | HCl | |
| 5.4 | 2-Cl | H | $CH_2OCH_3$ | H | 3-$CF_3$ | H | — | |
| 5.5 | 6-Cl | H | $CH_2OCH_3$ | 2-Cl | 4-Cl | H | — | |
| 5.6 | 6-Cl | $CH_3$ | $CH_3$ | H | 4-Cl | H | — | |
| 5.7 | 6-Cl | $CH_3$ | $C_2H_5$ | H | 3-$CF_3$ | H | — | |
| 5.8 | 6-Cl | H | $C_3H_7$—n | H | 4-$CH_3$ | H | $HNO_3$ | |
| 5.9 | 6-$CH_3$ | H | $CH_2OCH_3$ | 2-Cl | 4-Cl | H | — | |
| 5.10 | 6-Cl | $CH_3$ | $CH_3$ | 2-Cl | 4-Cl | H | — | resin |
| 5.11 | 6-$CH_3$ | H | $CH_2C_6H_5$ | H | 4-Cl | H | — | |
| 5.12 | 6-$OCH_3$ | H | $CH_2OH$ | H | 4-F | H | — | |
| 5.13 | 6-$OCH_3$ | $CH_3$ | $CH_3$ | 2-Cl | 4-Cl | H | — | |
| 5.14 | 6-$OCH_3$ | $CH_3$ | $C_2H_5$ | 2-Cl | 4-Cl | $CH_3$ | — | |
| 5.15 | 2-Cl | —$(CH_2)_4$— | | 2-Cl | 4-Cl | H | — | |
| 5.16 | 6-Cl | —$(CH_2)_4$— | | H | 4-F | H | — | |
| 5.17 | 6-$CH_3$ | —$(CH_2)_4$— | | H | 4-Cl | H | — | |
| 5.18 | 6-$OCH_3$ | —$(CH_2)_4$— | | H | 3-$CF_3$ | H | — | |
| 5.19 | 2-Cl | H | $CH_2Cl$ | 2-Cl | 4-Cl | H | $HNO_3$ | |
| 5.20 | 6-Cl | H | $CH_2Cl$ | 2-Cl | 4-Cl | H | — | |
| 5.21 | 6-$OCH_3$ | H | $CH_2Cl$ | 2-Br | 4-Br | H | — | |
| 5.22 | 6-$CH_3$ | H | $CH_2Cl$ | H | 4-Cl | H | — | |
| 5.23 | 2-Cl | H | $CH_2Cl$ | 2-Cl | 4-Cl | $C_2H_5$ | — | |
| 5.24 | 6-Cl | H | $CH_2Cl$ | 2-Cl | 4-Cl | $CH_2[C_6H_3(Cl_2)2,4]$ | — | |

TABLE 5-continued

Compounds of the formula

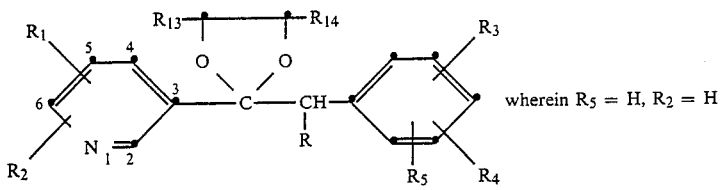 wherein $R_5 = H$, $R_2 = H$

| Comp. No. | $R_1$ | $R_{13}$ | $R_{14}$ | $R_3$ | $R_4$ | R | Salt | Physical constants |
|---|---|---|---|---|---|---|---|---|
| 5.25 | 2-Cl | H | $CH_2Cl$ | 2-Cl | 4-Cl | $C_6H_5$ | — | |
| 5.26 | 6-$OCH_3$ | H | $C_2H_5$ | 2-Cl | 4-Cl | cyclohexyl | — | |
| 5.27 | 2-Cl | $CH_3$ | H | 2-Cl | 4-Cl | H | — | resin |
| 5.28 | 2-Cl | $CH_2Cl$ | H | 2-Cl | 4-Cl | H | — | resin |
| 5.29 | 2-Cl | $CH_2OH$ | H | 2-Cl | 4-Cl | H | — | resin |
| 5.30 | 2-Cl | $CH_2Cl$ | H | 2-Cl | 4-Cl | $CH_3$ | — | resin |
| 5.31 | 6-Cl | $CH_3$ | H | 2-Cl | 4-Cl | H | — | resin |
| 5.32 | 6-Cl | $CH_2OH$ | H | 2-Cl | 4-Cl | H | — | resin |
| 5.33 | 6-Cl | $CH_2Cl$ | H | 2-Cl | 4-Cl | H | — | resin |
| 5.34 | 6-Cl | $CH_2Cl$ | H | 2-Cl | 4-Cl | $CH_3$ | — | resin |
| 5.35 | 6-Cl | $CH_2Cl$ | H | 2-Cl | 4-Cl | $CH_2C_6H_5$ | — | resin |

TABLE 6

Compounds of the formula

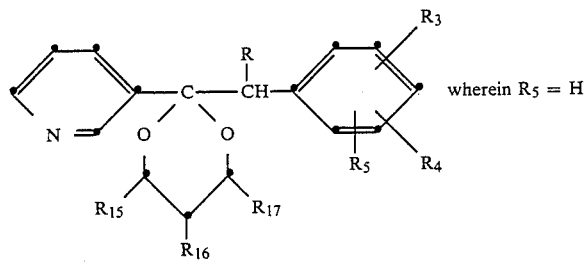 wherein $R_5 = H$

| Comp. No. | $R_{15}$ | $R_{16}$ | $R_{17}$ | $R_3$ | $R_4$ | R | Salt | Physical constants |
|---|---|---|---|---|---|---|---|---|
| 6.1 | $CH_3$ | H | H | 2-Cl | 4-Cl | H | — | |
| 6.2 | H | $CH_3$ | H | 2-Cl | 4-Cl | H | HCl | |
| 6.3 | H | $CH_3$ | $CH_3$ | 2-Cl | 4-Cl | H | — | |
| 6.4 | $CH_3$ | $CH_3$ | $CH_3$ | 2-Cl | 4-Cl | H | — | |
| 6.5 | H | H | H | 2-Cl | 4-Cl | H | — | m.p. 82-84° C. |
| 6.6 | H | $C_2H_5$ | H | H | 4-F | H | — | |
| 6.7 | $CH_3$ | $CH_3$ | H | H | 3-$CF_3$ | H | — | |
| 6.8 | $C_2H_5$ | H | H | 2-Cl | 4-Cl | H | — | |
| 6.9 | $C_2H_5$ | H | H | H | 4-$CH_3$ | H | — | |
| 6.10 | $C_3H_7$—n | H | $C_3H_7$—n | H | 4-F | H | — | |
| 6.11 | $C_2H_5$ | H | $C_2H_5$ | H | 4-Cl | H | — | |
| 6.12 | H | H | $C_4H_9$—n | 2-Cl | 4-Cl | H | $HNO_3$ | |
| 6.13 | H | $C_3H_7$—i | $CH_3$ | H | 4-$C_6H_5$ | H | — | |
| 6.14 | $CH_3$ | H | H | 2-Cl | 4-Cl | —$CH_3$ | — | |
| 6.15 | $CH_3$ | H | H | 2-Cl | 4-Cl | $CH_2[C_6H_3Cl_2(2,4)]$ | — | |
| 6.16 | H | H | $CH_3$ | 2-Cl | 4-Cl | cyclohexyl | — | |
| 6.17 | $C_2H_5$ | H | H | 2-Cl | 4-Cl | $C_6H_5$ | — | |
| 6.18 | $C_2H_5$ | H | H | 2-Cl | 4-Cl | $C_6H_{12}$—n | — | |
| 6.19 | H | H | H | 2-Cl | 4-Cl | $CH_3$ | — | resin |
| 6.20 | H | H | H | 2-Cl | 4-Cl | $C_3H_7$—n | — | resin |
| 6.21 | H | H | H | 2-Cl | 4-Cl | H | $HNO_3$ | m.p. 138-140° C. |

TABLE 7

Compounds of the formula

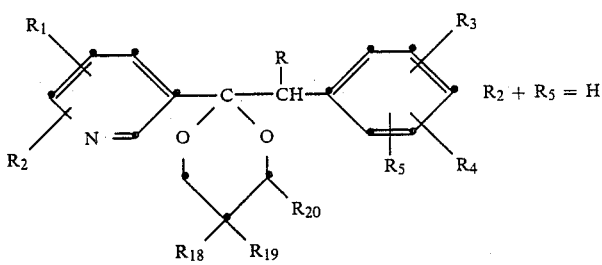

$R_2 + R_5 = H$

| Comp. No. | $R_1$ | $R_{18}$ | $R_{19}$ | $R_{20}$ | $R_3$ | $R_4$ | R | Physical constants |
|---|---|---|---|---|---|---|---|---|
| 7.1 | 2-Cl | H | H | $CH_3$ | 2-Cl | 4-Cl | H | |
| 7.2 | H | $CH_3$ | $CH_3$ | H | 2-Cl | 4-Cl | H | |
| 7.3 | H | $CH_3$ | $C_2H_5$ | H | 2-Cl | 4-Cl | H | |
| 7.4 | H | $CH_3$ | $CH_3$ | $CH_3$ | H | $4-C_6H_5$ | $CH_3$ | |
| 7.5 | 6-Cl | H | H | $CH_3$ | 2-Cl | 4-Cl | $C_3H_7-i$ | |
| 7.6 | 2-$OCH_3$ | $CH_3$ | $CH_3$ | H | H | H | H | |
| 7.7 | H | $C_2H_5$ | $C_2H_5$ | H | H | $3-CF_3$ | $C_6H_5$ | |
| 7.8 | 6-Cl | H | H | $CH_3$ | H | $3-CF_3$ | H | |
| 7.9 | 2-$CH_3$ | $CH_3$ | $CH_3$ | H | H | $3-NO_2$ | $CH_2C_6H_5$ | |
| 7.10 | H | $CH_3$ | $CH_3$ | H | 2-F | H | H | |
| 7.11 | 2-Cl | H | H | H | 2-Cl | 4-Cl | H | resin |
| 7.12 | 6-Cl | H | H | $CH_3$ | 2-Cl | 4-Cl | H | resin |
| 7.13 | 6-Cl | H | H | H | 2-Cl | 4-Cl | H | resin |

Formulation Examples for liquid active ingredients of the formula I (%=per cent by weight)

| F1. Emulsion concentrates | (a) | (b) | (c) |
|---|---|---|---|
| active ingredient from the Tables | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| F2. Solutions | (a) | (b) | (c) | (d) |
|---|---|---|---|---|
| active ingredient from the Tables | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

(M.W. = molecular weight)

The solutions are suitable for application in the form of very fine drops.

| F3. Granulates | (a) | (b) |
|---|---|---|
| active ingredient from Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4: Dusts | (a) | (b) |
|---|---|---|
| active ingredient from the Tables | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=per cent by weight)

| F5: Wettable powders | (a) | (b) | (c) |
|---|---|---|---|
| active ingredient from the Tables | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives, and the mixture is thoroughly ground in a suitable mill. Wettable powders which can be diluted with water to give suspensions of the required concentration are obtained.

| F6: Emulsion concentrate | |
|---|---|
| active ingredient from the Tables | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| F7: Dusts | (a) | (b) |
|---|---|---|
| active ingredient from the Tables | 5% | 8% |
| talcum | 95% | — |
| kaolin | — | 92% |

Dusts ready for use are obtained by mixing the active ingredient with the carriers and grinding the mixture in a suitable mill.

| F8: Extruder granulate | |
|---|---|
| active ingredient from the Tables | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| F9: Coated granulate | |
|---|---|
| active ingredient from the Tables | 3% |
| polyethylene glycol (M.W. 200) | 3% |
| kaolin | 94% |
| (M.W. = molecular weight) | |

The finely ground active ingredient is evenly applied, in a mixer, to the kaoline moistened with polyethylene glycol. Dustfree coated granules are obtained in this manner.

| F10: Suspension concentrate | |
|---|---|
| active ingredient from the Tables | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

Example B1: Action against Puccinia graminis on wheat (a) Residual-protective action Six days after being sown, wheat plants are sprayed with a spray liquor prepared from wettable powder of the active ingredient (0.06% of active ingredient). After 24 hours, the treated plants are infested with a uredospore suspension of the fungus. After an incubation time of 48 hours at about 20° C. with 95-100% relative humidity, the infested plants are kept in a greenhouse at about 22° C. An assessment of the development of rust pustules is made 12 days after infestation.

(b) Systematic action

A spray liquor prepared from wettable powder of the active ingredient (0.006% of active ingredient, relative to the volume of soil) is poured onto the soil of wheat plants 5 days after sowing. After 48, hours the treated plants are infested with a uredospore suspension of the fungus. After an incubation time of 48 hours at about 20° C. with 95-100% relative humidity, the infested plants are kept in a greenhouse at about 22° C. An assessment of the development of rust pustules is made 12 days after infestation.

Compounds listed in the Tables exhibit against Puccinia fungus a good action. Untreated but infested control plants display a level of Puccinia infection of 100%. Among other compounds giving good results, the compounds Nos. 2.1, 2.25 to 2.27 and 2.38 to 2.40 reduce Puccinia infection to 0 to 5%.

Example B2: Action against Cercospora arachidicola on groundnut plants (a) Residual-protective action Groundnut plants 10-15 cm in height are sprayed with a spray liquor produced from wettable powder of the active ingredient (0.02% of active ingredient); and 48 hours later they are infested with a conidiospore suspension of the fungus. The infested plants are incubated for 72 hours at about 21° C. with high relative humidity, and are subsequently kept in a greenhouse until the typical leaf spots have appeared. The assessment of the fungicidal action is made 12 days after infestation, and is based on the number and size of the occurring spots.

(b) Systemic action

A spray liquor prepared from wettable powder of the active ingredient (0.06% of active ingredient, relative to the volume of soil) is poured onto the soil of groundnut plants 10-15 cm in height. After 48 hours, the treated plants are infested with a conidiospore suspension of the fungus, and are subsequently incubated for 72 hours at about 21° C. with high relative humdity. The plants are then kept in a greenhouse, and an assessment of the extent of fungus infection is made after 11 days.

Compared with untreated, but infested control plants (number and size of spots=100%), groundnut plants which have been treated with the active ingredients from the Tables exhibit a greatly reduced level of Cercospora infection. Thus, the compounds Nos. 2.1, 2.6, 2.16, 2.25 to 2.28, 2.34, 2.38 to 2.40, 3.7, 3.8 and 6.5 prevent the occurrence of spots in the above tests almost completely (0-10%).

Example B3: Action against Erysiphae graminis on barley (a) Residual-protective action Barley plants about 8 cm in height are sprayed with a spray liquor prepared from wettable powder of the active ingredient (0.02% of active ingredient). After 3-4 hours, the treated plants are dusted with conidiospores of the fungus. The infested barley plants are kept in a greenhouse at about 22° C., and the extent of fungus infection is assessed after 10 days.

(b) Systemic action

A spray liquor prepared from wettable powder of the active ingredient (0.006% of active ingredient), relative to the volume of soil) is poured into the soil of barley plants about 8 cm in height. Care is taken to ensure that the spray liquor does not come into contact with the parts of the plants above the soil. After 48 hours, the treated plants are dusted with conidiospores of the fungus. The infested barley plants are kept in a greenhouse at about 22° C., and an assessment of the extent of fungus infection is made after 10 days.

Compounds of the formula I exhibit a good action against Erysiphe fungus. Untreated but infested control plants display a level of Erysiphe infection of 100%. Among other effective compounds shown in the Tables, the compounds Nos. 2.1, 2.6, 2.12, 2.16, 2.25 to 2.28, 2.34, 2.35, 2.37 to 2.40, 3.7, 3.8, 5.10, 5.28 to 5.30, 5.32 to 5.34, 6.5, 6.19 and 6.21 reduce fungus infection on barley to 0 to 5%.

Example B4: Residual-protective action against Venturi inaequalis on apple shoots Apple seedlings having 10-20 long fresh shoots are sprayed with a spray liquor prepared from wettable powder of the active ingredient (0.06% of active ingredient). The treated plants are sprayed after 24 hours with a conidiospore suspension of the fungus. The plants are then incubated for 5 days with 90-100% relative humidity, and for a further 10 days they are kept at 20°-24° C. in a greenhouse. The extent of scab infection is assessed 15 days after infestation.

Compounds from the Tables reduce infection to less than 10%, whereas untreated but infested control shoots suffer a 100% level of infection.

Example B5: Action against Botrytis cinerea on beans

Residual-protective action

Bean plants about 10 cm in height are sprayed with a spray liquor prepared from wettable powder of the active ingredient (0.02% of active ingredient). The plants are infested after 48 hours with a conidiospore suspension of the fungus. The extent of fungus infection is assessed after incubation of the infested plants for 3 days at 21° C. with 95-100% relative humidity.

The compounds from the Tables very greatly reduce fungus infection in many cases, particularly the compounds Nos. 2.1, 2.6, 2.12, 2.16, 2.25, 2.26, 2.27, 2.28, 2.34, 2.38 to 2.40, 3.8 and 6.5.

What is claimed is:

1. A compound of the formula or an acid addition salts thereof, wherein
R is hydrogen, $C_1$-$C_6$-alkyl, $C_3$-$C_6$-cycloalkyl, phenyl, benzyl, phenyl substituted by $C_1$-$C_4$alkyl, halogen, $C_1$-$C_4$-alkoxy, $NO_2$ or $CF_3$, or benzyl substituted by $C_1$-$C_4$-alkyl, halogen, $C_1$-$C_4$-alkoxy, $NO_2$ and/or $CF_3$,
$R_1$ and $R_2$ independently of one another are each hydrogen, $C_1$-$C_4$-alkyl, halogen or $C_1$-$C_4$-alkoxy,
$R_3$, $R_4$ and $R_5$ independently of one another are each hydrogen, halogen, $CF_3$, $NO_2$, $C_1$-$C_4$-alkyl, $C_1$-$C_4$-alkoxy, phenyl, or phenyl substituted by $C_1$-$C_4$-alkyl, $C_1$-$C_4$-alkoxy, halogen, $NO_2$ or $CF_3$, U and V together form the following alkylene bridge in which $R_g$ is hydrogen or $C_1$-$C_4$-alkyl.

2. A compound according to claim 1 wherein R is hydrogen or methyl, $R_1$ and $R_2$ independently of one another are each hydrogen, methyl, ethyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy.

3. A compound according to claim 2 wherein R is hydrogen, $R_1$ and $R_2$ independently of one another are each hydrogen, methyl, fluorine, chlorine, bromine or methoxy, $R_3$, $R_4$ and $R_5$ independently of one another are each hydrogen, fluorine, chlorine, bromine, $CF_3$, $NO_2$, methyl or methoxy.

4. A compound selected from the group consisting of:
3-[2-(2,4-dichlorobenzyl)-4-methoxymethyl-1,3-dioxolan-2-yl]-pyridine,
3-[2-(2,4-dichlorobenzyl)-4-chloromethyl-1,3-dioxolan-2-yl]-pyridine, and
3-[2-(2,4-dichlorobenzyl)-4-hydroxymethyl-1,3-dioxolan-2-yl]-pyridine.

5. A compound selected from the group consisting of:
3-[2-(2,4-dichlorobenzyl)-4-chloromethyl-5-methyl-1,3-dioxolan-2-yl]-pyridine, and
3-[2-(2,4-dichlorobenzyl)-4-hydroxymethyl-5-methyl-1,3-dioxolan-2-yl]-pyridine.

6. A fungicidal composition for controlling or preventing an infestation by fungi, which composition contains, as at least one active ingredient, a fungicidally effective amount of a compound of claim 1, together with a carrier.

7. A fungicidal composition for controlling or preventing an infestation by fungi, which composition contains, as at least one active ingredient, a fungicidally effective amount of a compound of claim 4 together with a carrier.

8. A fungicidal composition for controlling or preventing an infestation by fungi, which composition contains, as at least one active ingredient, a fungicidally effective amount of a compound of claim 5, together with a carrier.

9. A method of controlling or preventing an infestation of cultivated plants by phytopathogenic microorganisms, which process comprises applying to the plants or to the locus thereof a compound of claim 1 in an amount effective to control said microorganisms or prevent infestation thereby.

10. A method of controlling or preventing an infestation of cultivated plants by phytopathogenic microorganisms, which process comprises applying to the plants or to the locus thereof a compound of claim 4 in an amount effective to control said microorganisms or prevent infestation thereby.

11. A method of controlling or preventing an infestation of cultivated plants by phytopathogenic microorganisms, which process comprises applying to the plants or to the locus thereof a compound of claim 5 in an amount effective to control said microorganisms or prevent infestation thereby.

* * * * *

UNITED STATES PATENT AND TRADEMARK OFFICE
CERTIFICATE OF CORRECTION

PATENT NO. : 4,859,687
DATED : Aug. 22, 1989
INVENTOR(S) : Peter Riebli

It is certified that error appears in the above-identified patent and that said Letters Patent is hereby corrected as shown below:

ON TITLE PAGE:

Line [73] Should read:

Assignee: Ciba-Geigy Corporation, Ardsley, N.Y.

Signed and Sealed this

Twenty-second Day of October, 1991

*Attest:*

HARRY F. MANBECK, JR.

*Attesting Officer*      *Commissioner of Patents and Trademarks*